United States Patent
Murphy

Patent Number: 5,902,308
Date of Patent: May 11, 1999

[54] LESION DIAMETER MEASUREMENT CATHETER AND METHOD

[75] Inventor: Richard Murphy, Mountain View, Calif.

[73] Assignee: Medtronic, Inc., Minneapolis, Minn.

[21] Appl. No.: 08/895,933

[22] Filed: Jul. 17, 1997

Related U.S. Application Data

[62] Division of application No. 08/435,288, May 4, 1995, Pat. No. 5,752,522.

[51] Int. Cl.⁶ .................................................. A61F 11/00
[52] U.S. Cl. ...................... 606/108; 606/191; 606/194; 128/774
[58] Field of Search ................................. 606/108, 191, 606/192, 194; 128/774, 673

[56] References Cited

U.S. PATENT DOCUMENTS

| | | | |
|---|---|---|---|
| 4,564,014 | 1/1986 | Fogarty et al. | 128/344 |
| 4,651,738 | 3/1987 | Demer et al. | 128/344 |
| 4,873,989 | 10/1989 | Einzig | 128/692 |
| 5,045,071 | 9/1991 | McCormick et al. | 604/280 |
| 5,135,488 | 8/1992 | Foote et al. | 604/97 |
| 5,146,922 | 9/1992 | Williamson et al. | 128/774 |
| 5,171,299 | 12/1992 | Heitzmann et al. | 604/100 |
| 5,209,730 | 5/1993 | Sullivan | 604/96 |
| 5,219,355 | 6/1993 | Parodi et al. | 606/191 |
| 5,239,982 | 8/1993 | Trauthen | 128/4 |
| 5,263,928 | 11/1993 | Trauthen et al. | 604/53 |
| 5,275,169 | 1/1994 | Afromowitz et al. | 128/673 |
| 5,316,016 | 5/1994 | Adams et al. | 128/774 |
| 5,343,874 | 9/1994 | Picha et al. | 128/780 |
| 5,364,354 | 11/1994 | Walker et al. | 604/96 |
| 5,382,261 | 1/1995 | Palmaz | 606/158 |
| 5,419,324 | 5/1995 | Dillow | 128/653.1 |
| 5,431,628 | 7/1995 | Millar | 604/100 |
| 5,465,732 | 11/1995 | Abele | 128/772 |
| 5,484,449 | 1/1996 | Amundson et al. | 606/108 |
| 5,499,995 | 3/1996 | Teirstein | 606/192 |

FOREIGN PATENT DOCUMENTS

| | | | |
|---|---|---|---|
| 2 137 499 | 10/1984 | United Kingdom | A61B 1/00 |
| WO 95/14501 | 6/1995 | WIPO | A61M 29/00 |
| WO 95/28885 | 11/1995 | WIPO | A61B 17/00 |

OTHER PUBLICATIONS

Chuter, T. et al., "Anatomy of the Infrarenal Aortic Aneurysm," *Endoluminal Vascular Prostheses*, pp. 21–36, Little, Brown and Company, Boston (1995).

Chuter, T. et al., "Patient Selection and Preoperative Assessment," *Endoluminal Vascular Prostheses*, pp. 255–283, Little, Brown and Company, Boston (1995).

Demer, Linda L., et al., "High Intensity Ultrasound Increases Distensibility of Calcific Atherosclerotic Arteries," *J Am Coll Cardiol*, 18:1259–1262, Nov. 1991.

Nichols, Allen B., et al., "Quantification of Relative Coronary Arterial Stenosis by Cinevideodensitometric Analysis of Coronary Arteriograms," *Circulation*, 69:512–522, 1984.

Serruys, Patrick W. et al., "Assessment of Percutaneous Transluminal Coronary Angioplasty by Quantitative Coronary Angiography: Diameter Versus Densitometric Area Measurements," *Am J. Cardiol* 54:482–488, 1984.

Abele, John E., "Balloon Catheters and Transluminal Dilation: Technical Considerations," *AJR* 135:901–906, Nov. 1980.

*Primary Examiner*—Michael Buiz
*Assistant Examiner*—Daphna Shaz
*Attorney, Agent, or Firm*—Townsend and Townsend and Crew LLP

[57] ABSTRACT

The invention provides methods and apparatus for determining cross-sectional dimensions of body lumens, such as the diameter of a blood vessel. According to one exemplary method, the diameter of a blood vessel is measured by first inflating a balloon catheter within the lumen until the balloon diameter matches the lumen diameter. Inflation may be at a very low pressure and be constrained by the lumen, or may alternatively be controlled by monitoring the flow within the lumen. The balloon includes at least one measurement element which indicates the expanded balloon cross-sectional area, circumference, or diameter. Optionally, the measurement element provides a fluoroscopic, radiographic, or ultrasound indication of the cross-sectional dimension. In alternative embodiments, such dimensions may be transmitted to the distal end of the catheter, or determined after deflation and removal of the catheter.

8 Claims, 8 Drawing Sheets

LESION DIAMETER MEASUREMENT CATHETER AND METHOD

This is a Division of application Ser. No. 08/435,288, filed May 4, 1995 U.S. Pat. No. 5,752,522.

BACKGROUND OF THE INVENTION

1. Field of the Invention

The present invention relates generally to the field of medical diagnostics, and particularly to the field of determining physiologic characteristics of body lumens. In one particular aspect, the invention provides methods and apparatus for measuring the cross-section of a diseased vessel segment.

To properly treat many bodily diseases or abnormalities, certain physiologic characteristics, such as the size of a particular body member, often need to be determined. One example is in the treatment of vascular lesions, stenosed regions, and particularly vascular aneurysms, which often requires the endoluminal placement of tubular prostheses, such as grafts, stents, and other structures. Before the prothesis is placed in the vascular anatomy, the size of the lesion is measured so that a properly sized prosthesis can be selected.

Vascular aneurysms are defined as the abnormal dilation of a blood vessel, usually resulting from disease and/or genetic predisposition which can weaken the arterial wall and allow it to expand. While aneurysms can occur in any blood vessel, most occur in the aorta and peripheral arteries, with the majority of aortic aneurysms occurring in the abdominal aorta, usually beginning below the renal arteries and often extending distally into one or both of the iliac arteries.

Aortic aneurysms are most commonly treated in open surgical procedures where the diseased vessel segment is by-passed and repaired with an artificial vascular graft. Recently, methods for endovascular graft placement for the treatment of aneurysms have been proposed. One such method and apparatus for endovascular placement of intraluminal prostheses, including both grafts and stents, is described in co-pending U.S. patent application Ser. No. 08/290,021, filed Aug. 12, 1994, the disclosure of which is herein incorporated by reference. A suitable intraluminal prosthesis for such a method includes a radially compressible, tubular frame having a proximal end, a distal end, and an axial lumen therebetween. The prosthesis is delivered to the area of interest via a delivery catheter. The prosthesis is then partially released from the catheter into a blood vessel or other body lumen to allow the prosthesis to radially expand and conform to the interior surface of the lumen being treated. The prosthesis can then be repositioned by the catheter until it is properly placed within the vessel. Optionally, the prosthesis may be implanted within a vessel by expanding a malleable portion of the prosthesis with a balloon catheter. Exemplary graft prostheses are described in co-pending U.S. patent application Ser. No. 08/255,681, the disclosure of which is herein incorporated by reference.

As previously described, before the endoluminal placement of an intraluminal prosthesis, it is desirable to first determine the appropriate size for the expanded prosthesis so that the prosthesis will properly fit within the body lumen. For instance, in the case of vascular aneurysms, it is often desirable to determine the diameter of the vessel adjacent to the aneurysm so that the prosthesis will match the size of the vessel on either side of the diseased area. In other circumstances, the cross-sectional area or the circumference of a lumen would be helpful. For example, where a prosthesis will conform to a vessel which has an irregular cross-section, it is desirable that the periphery of the implanted prosthesis match the lumen circumference to seal along the periphery. Alternatively, the open cross-section area would be helpful in determining whether placement of a prosthesis is an appropriate therapy for a stenosed lumen. As a final example, it is desirable to select a properly sized balloon catheter to firmly implant the prosthesis within the vessel, but which will not over-expand the prosthesis and damage the healthy vessel walls.

Current methods for measuring the open cross section near an effected body lumen employ fluoroscopy. To determine the diameter of a vessel using fluoroscopy, a catheter is inserted into the vessel and a contrast agent is injected into the vessel through the catheter. The blood flow carries the contrast agent along the vessel so that the vessel can be radiographically imaged with a fluoroscope. The fluoroscope produces a planar (or two dimensional) image of the vessel which can be evaluated to determine the existence of a diseased or abnormal area within the vessel. The nominal diameter of the diseased or abnormal area is then estimated by measuring the diameter of the vessel in the area adjacent to the diseased area on the radiographic image. However, such a measurement is typically not particularly accurate since it relies on discerning an ill-defined boundary in a single plane. Such a measurement does not take into account that the vessel is usually not in the same plane as the resulting fluoroscopic image. Another drawback to such procedures in determining the diameter of a vessel is that the vessel is often irregular in cross section, i.e., is not circular. Hence, even if the vessel were in the same plane as the resulting fluoroscopic image of the vessel, it would still be difficult to measure the open diameter of an irregular vessel.

Alternative prior art methods for measuring physiological characteristics of lumens have stressed the diseased lumen being measured. To determine lumen wall compliance and internal diameter, it has been proposed that a balloon be inflated with relatively low pressure fluid within a lumen. By monitoring inflation fluid volume and pressure, wall compliance of an expanding lumen can be determined. By inflating the balloon with sufficient internal pressure to expand the balloon so that it is restrained by the lumen wall, lumen cross-sectional area or diameter can also be measured. However, the balloon must be inflated with sufficient pressure to ensure that it has contacted the lumen wall all along the periphery to obtain an accurate measurment. Additionally, the measurement balloon systems of the prior art have utilized generally cylindrical balloons of non-compliant materials. Hence, the prior art methods have stressed the target region of the diseased lumen by forcing irregular lumens towards a cylindrical shape and by distending the diseased lumen.

Improper determination of the vessel size can result in the selection of a prosthesis that is too small and hence cannot be properly grafted. The endoluminal placement of an improperly sized prosthesis can present a number of serious problems. One problem is that the prosthesis must be removed from the body lumen and replaced with another that is properly sized. This can often be difficult if the prosthesis has been radially expanded while in the body lumen. To remove the expanded prosthesis, the prosthesis must be radially compressed and then withdrawn from the body lumen. Such a procedure increases the risk of injury to the patient as well as unduly increasing operating time and expense.

Methods and apparatus are therefore needed for accurately measuring the cross-section of a body lumen, and in particular the diameter, circumference, and cross-sectional area of a vascular lesion. In one particular aspect, it would be desirable to provide improved methods and apparatus for the measurement of blood vessels in the region adjacent aneurysms so that the proper size of intraluminal prostheses, such as grafts and stents, can be accurately determined. It would be further desirable if such methods and apparatus were simple to use and could be used with existing fluoroscopy technology. Finally, it would be particularly desirable if such measurements could be taken without causing unnecessary stress to the diseased vessel.

2. Description of the Background Art

As previously described, methods and apparatus for placement and repositioning of intraluminal prostheses are described in U.S. patent application Ser. No. 08/290,021, the disclosure of which has previously been incorporated by reference. Suitable graft structures for placement in body lumens are described in U.S. patent application Ser. No. 08/255,681, the disclosure of which has previously been incorporated herein by reference.

U.S. Pat. No. 5,275,169 describes methods and apparatus for determining the internal cross-sectional area and compliance of a vessel by measuring the volume and pressure of an incompressible fluid within an inflated balloon catheter. U.S. Pat. No. 4,651,738 describes a system for monitoring the pressure-volume relationship during conventional angioplasty procedures. U.S. Pat. No. 5,171,299 describes a similar apparatus which displays balloon pressure and diameter based on internal balloon pressure during angioplasty. U.S. Pat. No. 5,135,488 describes an angioplasty system having a microprocessor for controlling, monitoring, displaying, and recording balloon inflation data. The medical literature also describes such measurements. See, for example, Abele (1980) *AJR* 135:901–906; Dembe et al. (1991) *J. Am. Coll. Cardiol.* 18:1259–1262. The use of computer enhanced radiographic imaging techniques for determining vascular lumen diameter is described in Serruys et al. (1984) *Am. J. Cardiol.* 54:482–488; and Nicols et al. (1984) *Circulation* 69:512–522.

SUMMARY OF THE INVENTION

The present invention provides methods and apparatus for determining a cross-sectional dimensions of body lumens, and particularly for determining the cross-sectional area, circumference and diameter of target regions within body lumens. Body lumens amenable to the methods and apparatus of the present invention include blood vessels, the intestines, the urethra, and the like. Although suitable for the measurement of most body lumens, the present invention will find its greatest use in the measurement of vascular lesions, particularly vascular aneurysms, vascular stenoses, and the like. Advantageously, the cross-sectional dimensions of such lesions can be used to select the proper size of intraluminal prostheses, such as grafts and stents, the proper balloon for balloon angioplasty procedures, and the proper therapy for that vascular lesion.

The methods of the present invention are carried out without disrupting the cross-sectional characteristics being determined. According to the present methods, a balloon catheter is inflated within a diseased lumen so that a cross-section of the balloon substantially matches the cross-section of the lumen being measured. The present methods then measure a cross-sectional dimension of the balloon within the lumen. As used herein, "cross-sectional dimension" includes all physical dimensions of the body lumen which relate or correspond to the cross-sectional area, specifically including the cross-sectional area, peripheral length (e.g. circumference), width (e.g. diameter in circular vessels), and the like. Advantageously, the present methods are performed without significantly distending the diseased lumen prior to selection and application of an appropriate therapy.

The present invention may advantageously be used with other apparatus and methods for measurement of the length of vascular lesions, as disclosed in copending U.S. patent application Ser. No. 08/380,735 (Attorney Docket No. 16380-16), the disclosure of which is herein incorporated by reference.

Broadly, the present method for measuring a cross-section of a lumen comprises inserting a balloon catheter into the lumen, and aligning the balloon with a target location of the lumen. The balloon is then inflated so that a cross-section of the balloon is substantially the same as the cross-section of the target location of the lumen. A cross-sectional dimension of the inflated balloon is then measured, providing the corresponding dimension of the target location of the lumen.

Advantageously, the methods of the present invention avoid the distending of the lumen required for the pressure/volume monitoring methods of the prior art. Instead, the present methods measure a lumen cross-sectional dimension from a balloon inflated so as to have a cross-section that is substantially the same as the lumen being measured, i.e. with minimal or no luminal distension. As used herein, "substantially the same" is used to mean that the balloon cross-section conforms to the lumen cross-section without substantially altering the cross-sectional shape or any cross-sectional dimension. Preferably, the balloon changes the measured cross-sectional width by less than 5%, ideally by less than 2%.

In one aspect of the present lumen measurement method, the peripheral surface of the balloon is conformed or matched to the lumen based on a change in a flow through the lumen. The change is preferably measured by a sensing a change in the flow as the balloon is expanded, preferably with a sensor on the catheter. The expansion can thus be terminated when, for example, the flow is substantially blocked by the balloon, before the balloon has applied any significant force against the lumen wall.

In certain embodiments of the present method, a very flexible elastomeric balloon is inflated using a low pressure fluid, expanding the balloon until it is restrained by the lumen wall. The fluid is at sufficiently low pressure that it will not distend the lumen wall, while the elastomeric material allows the balloon to expand to conform with an irregular lumen cross-section. Preferably, an external pressure sensor measures lumen ambient physiological pressure to limit the required inflation fluid pressure. The balloon thereby inflates so as to have substantially the same cross-section as the body lumen, without substantially expanding or otherwise traumatizing the body lumen.

Alternative embodiments of the present methods comprise expanding balloons having a conical or tapered shape with low pressure inflation fluid until a portion of the balloon having a cross-section smaller than the lumen is fully expanded, while a portion of the balloon having a cross-section larger than the lumen is not fully expanded. In such embodiments only a portion of the balloon is matched or conformed to the cross-section of the body lumen.

As described in more detail hereinbelow, there are several alternative methods for measuring the cross-section of the inflated balloon. In certain embodiments of the present method, a cross-sectional dimension of the lumen is found by deflating and removing the balloon, and measuring certain irreversible changes which were recorded during the maximum expansion of the balloon within the lumen. For example, a balloon having a plurality of internal segments, where each segment is attached to the inside of the balloon wall to define a balloon diameter, will record a lumen diameter by breaking those segments which are shorter than the maximum inflated balloon diameter.

Alternative embodiments of the present methods determine the expanded balloon cross-section in situ using remote electrical or mechanical indicators. For example, a conductive coil which expands with the balloon wall will vary in electrical characteristics in correlation with balloon cross-section. Hence, measuring the resistance, inductance, or capacitance of such an expanding conductive coil allows immediate calculation of the inflated balloon circumference or diameter.

In further alternative embodiments, measurement elements are interpreted in situ using known imaging modalities, such as fluoroscopy, radiography, ultrasound, or the like. For example, a balloon having elastomeric marker bands on the balloon wall are imaged while inflated to match the lumen cross-section. Preferably, the marker bands provide a sharp image, and increase in width in correlation with increasing balloon circumference, allowing calculation of the lumen circumference from the marker band width. Advantageously, such marker band widths could be accurately measured using known intravascular ultrasound (IVUS) systems from within a lumen of the catheter.

The lesion measurement catheters of the present invention comprise a catheter body having proximal and distal ends, and a balloon disposed at the distal end of the body. The present catheters will usually include means for matching an inflated diameter of the balloon with a diameter of a target location of a lumen, as described above. Preferably, the present catheters also include a measurement element for measurement of the inflated balloon.

Several alternative embodiments of the measurement element are described. In a preferred embodiment, the balloon is elastomeric and includes an external pressure sensor which indicates the pressure on the outer surface of the catheter. Optionally, an internal pressure sensor measures the pressure of an inflation fluid within the inflated balloon. The diameter of an elastomeric balloon can be correlated from a difference in these two pressures. Alternatively, monitoring the volume of an incompressible inflation fluid allows calculation of the cross-sectional area of the inflated balloon. Advantageously, the external pressure sensor can also measure changes in the flow through the lumen to indicate when the balloon has fully matched or conformed to the lumen cross-section, as described above.

In certain embodiments the measurement element will comprise marker bands to provide an indicator of the balloon's cross-section. Optionally, the marker bands are visible using known imaging techniques, including fluoroscopy, intravascular ultrasound (IVUS), and the like. Preferably, the marker bands are elastomeric and increase in width as the balloon expands, as described above. Alternatively, the marker bands are conductors which change in electrical property as the balloon expands.

Alternative embodiments of the present measurement catheter comprise a balloon and an electrical coil attached to the balloon wall so as to expand the coil as the balloon inflates. Electrical properties of such a coil will vary with balloon cross-sectional dimension.

Further alternative embodiments of the present catheter provide a mechanical measurement of the balloon diameter or circumference. Optionally, a linkage assembly expands to measure the internal balloon diameter. Alternatively, an inelastic coil which expands with the balloon will unwind with an increasing balloon circumference. Such mechanical measurements are optionally imaged using fluoroscopy, X-ray, or ultrasound, or alternatively are transmitted along the catheter body.

Still further embodiments of the present lesion measurement catheter include at least one measurement element which is altered by expansion of the balloon within the lumen. Optionally, a plurality of segments or disks corresponding to varying balloon diameters are provided, at least one corresponding to a diameter larger than the lumen and at least one corresponding to a diameter smaller than the lumen. The image of the segments or disks may change under fluoroscopy or ultrasound when a balloon diameter exceeds a corresponding segment or disk diameter. Alternatively, irreversibly overexpanded segments or disks may record the maximum expanded diameter of the balloon after the catheter has been deflated and removed.

DETAILED DESCRIPTION OF THE SPECIFIC EMBODIMENT

The present invention provides methods and apparatus for determining cross-sectional dimensions, such as the internal diameter, circumference, or cross-sectional area, of a body lumen. The methods and apparatus will preferably be used to measure the cross-section of vascular lesions, and will find its greatest use in measuring the diameter of vascular aneurysms and stenoses. The methods and apparatus can also find use in measuring internal dimensions of other defects or abnormalities. Diameter and peripheral lengths provided by the present invention will be particularly useful in sizing intraluminal prostheses, such as vascular grafts or stents, that are endovascularly placed within the vessel to treat the aneurysm or other abnormality. Cross-sectional areas provided by the invention can also be used to select the proper diameter for a balloon angioplasty catheter or to size other therapeutic devices.

An important feature of the present invention is that it allows cross-sectional dimensions to be measured regardless of the orientation of the body lumen within the body. Usually, most body lumens curve throughout the body thereby reducing the accuracy of measurements obtained from conventional fluoroscopy procedures which produce planar images of the lumen. The present invention takes into consideration both the varied orientations of body lumens within the body and their irregular cross-sectional shapes when determining their physiologic characteristics. In making such determinations, the present invention can incorporate the use of existing fluoroscopy technology as well as existing ultrasonic imaging technology.

An advantage of the present invention is that the distending of the abnormal or diseased body lumen, as associated with prior art lumen diameter measurements, is avoided. Instead, a cross-section of the present balloon catheter is matched with the lumen diameter. The balloon cross-sectional dimension can then be determined, indirectly providing the lumen diameter. Thus, a proper therapy can be selected based on the existing dimensions of the lumen, before those dimensions are altered.

Figure 1:
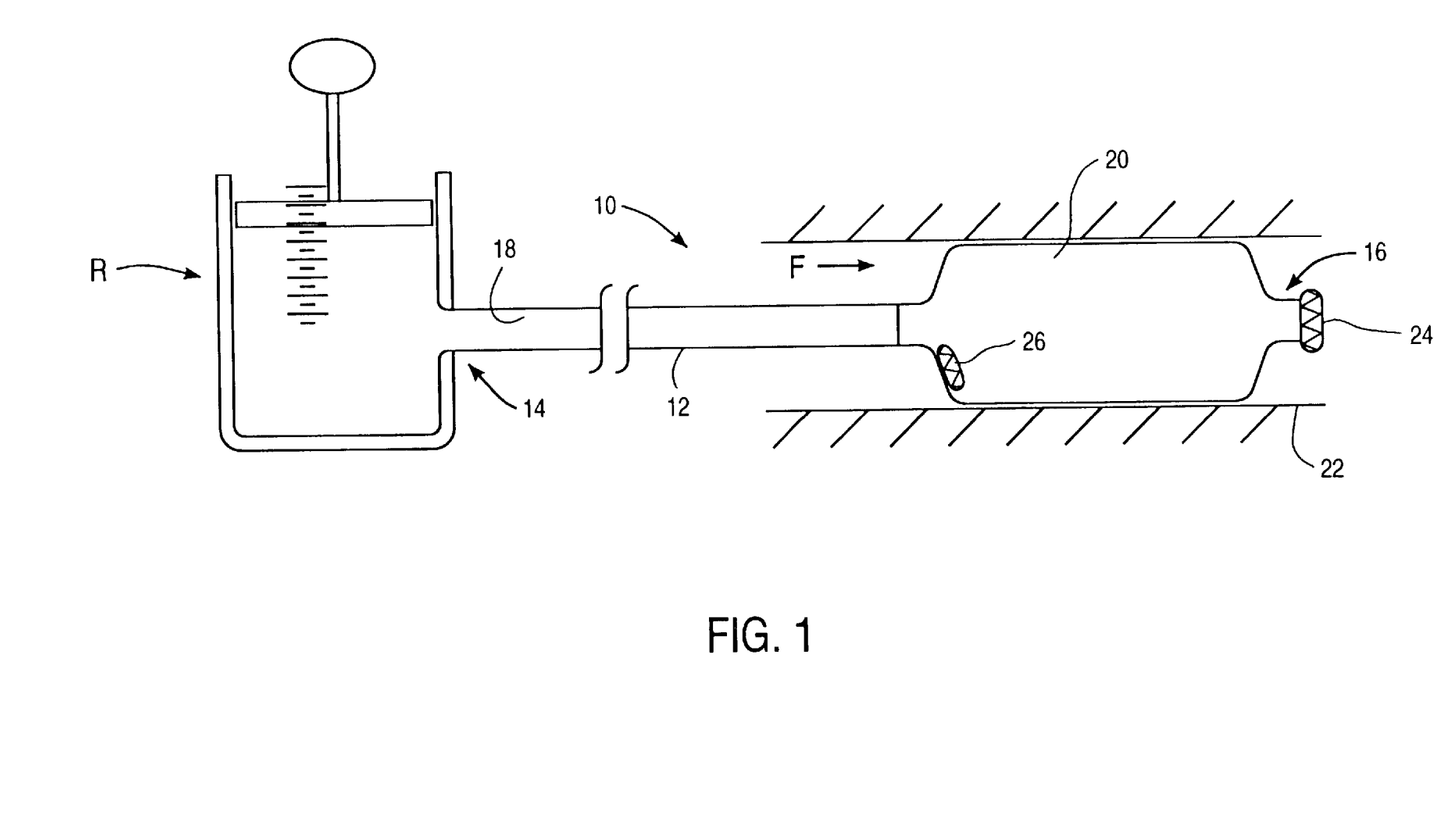
FIG. 1 is a schematic illustration of a first embodiment of a lumen measurement catheter according to the present invention. The catheter is shown with the balloon inflated within a body lumen.

To provide such features and advantages, the invention in one exemplary embodiment provides a luminal lesion measurement catheter 10 as shown in FIG. 1. The catheter 10 includes an elongate tubular body 12 having a proximal end 14, a distal end 16, and a lumen 18 therebetween. Preferably, the length of tubular body 12 will be in the range from about 40 cm to about 200 cm. A balloon 20 is disposed about tubular body 12 near distal end 16. Balloon 20 usually comprises an elastomeric material such as latex. In some embodiments, balloon 20 may alternatively comprise a flexible, inelastic material such as polyurethane, PET, or the like. Catheter 10 is seen in FIG. 1 inserted into a body lumen 22, with balloon 20 shown in an inflated configuration. Balloon 20 is expandable within lumen 22 so that the balloon cross-section matches and conforms to the lumen cross-section, but need not stress lumen 22 by expanding substantially beyond that point. In this embodiment, expansion is controlled using external sensor 24 attached to distal end 16 proximal of balloon 20. As balloon 20 expands, occlusion of the body lumen will cause a drop in pressure and a reduction in flow F. Sensor 24 may sense either pressure or flow. Regardless, the expansion of balloon 20 is terminated prior to expanding or stressing lumen 22.

Alternatively, expansion of the balloon may be stopped before the flow in the lumen is completely blocked, thereby avoiding all stress on the lumen wall, as well as the hazards of complete blockage of a lumen. Total lumen cross-section are then found by a correlation between the balloon diameter and the change in lumen flow, as measured at external sensor 24. Similarly, bypass flow lumens (not shown) of known size extending from the proximal end to the distal end of the balloon may alternatively be incorporated.

The diameter of inflated balloon 20 is then measured to determine the diameter of the lumen. The present invention provides several alternative embodiments of balloon diameter measurement elements or means. Preferably, balloon 20 comprises an elastomeric balloon having a known correlation between internal pressure and diameter. An internal pressure sensor 26 provides the internal balloon pressure, and thereby allows balloon diameter to be calculated from internal pressure. Preferably, internal pressure data is combined with external pressure from sensor 24 to provide the pressure difference across balloon 20. As the balloon diameter is most accurately determined by this difference in pressure, this combination provides a very precise indication of balloon diameter.

Optionally, monitoring the volume of an incompressible inflation fluid introduced into catheter 10 from calibrated reservoir R allows the present catheter system to measure both the cross-sectional area and compliance of lumen 22. Once balloon 20 has been matched to the lumen cross-section as described above, the cross-section of the balloon may be calculated from the inflation volume and the inflated balloon length. Clearly, such a calculation is most accurate where balloon 20 is constructed so as to expand radially only, rather than in length.

Further inflation of balloon 20 from calibrated reservoir R will expand the balloon outward against the lumen. Correlating the change in fluid volume of the balloon with the change in pressure (as measured at internal sensor 26) will allow calculation of the lumen wall resilience. An alternative apparatus and method for such a measurement is disclosed in U.S. Pat. No. 5,275,169.

Figure 2:
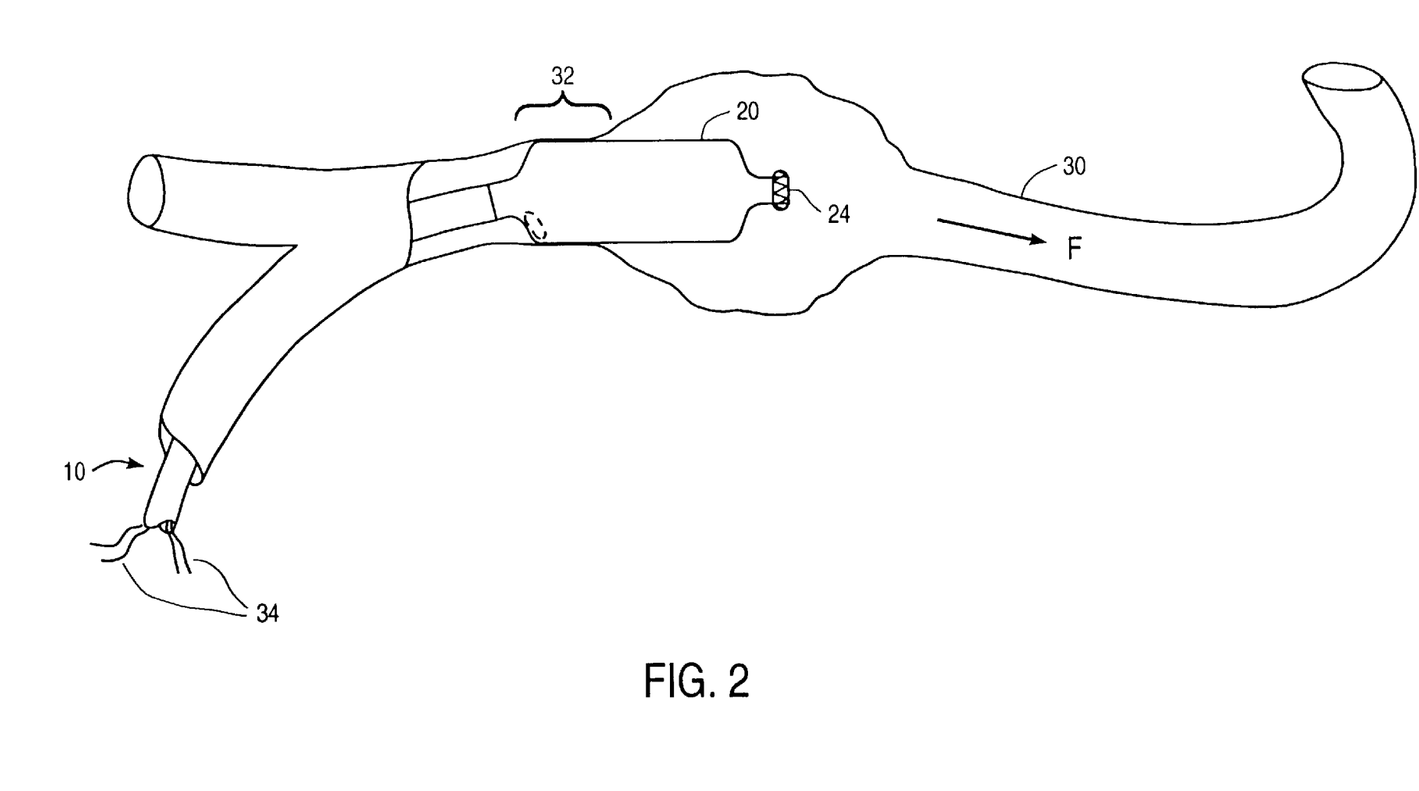
FIG. 2 illustrates the catheter of FIG. 1 in a measuring position.

FIG. 2 illustrates the lesion measurement catheter of FIG. 1 as used to measure a blood vessel cross-section in the region adjacent to an aneurism. Alternatively, the catheter might be used to measure the diameter of the aneurism itself, or to measure the open cross-sectional area of a stenosed region, or the like. Advantageously, the present devices and methods allow such measurements without distending or otherwise traumatizing such diseased lumens.

As shown in FIG. 2, catheter 10 has been inserted within an abnormal lumen 30 and aligned with a target region 32. The diameter of target region 32 might, for example, be needed to determine the size of an intraluminal stent to be inserted within lumen 30. Balloon 20 is shown inflated, thereby blocking a normal blood flow F. Thus the pressure and flow acting on external sensor 24 has been altered. This information is transmitted to the physician via wires 34. When flow F is completely blocked by balloon 20, the cross-section of balloon 20 has been matched to the cross-section of target region 32 of lumen 30.

Figure 3:
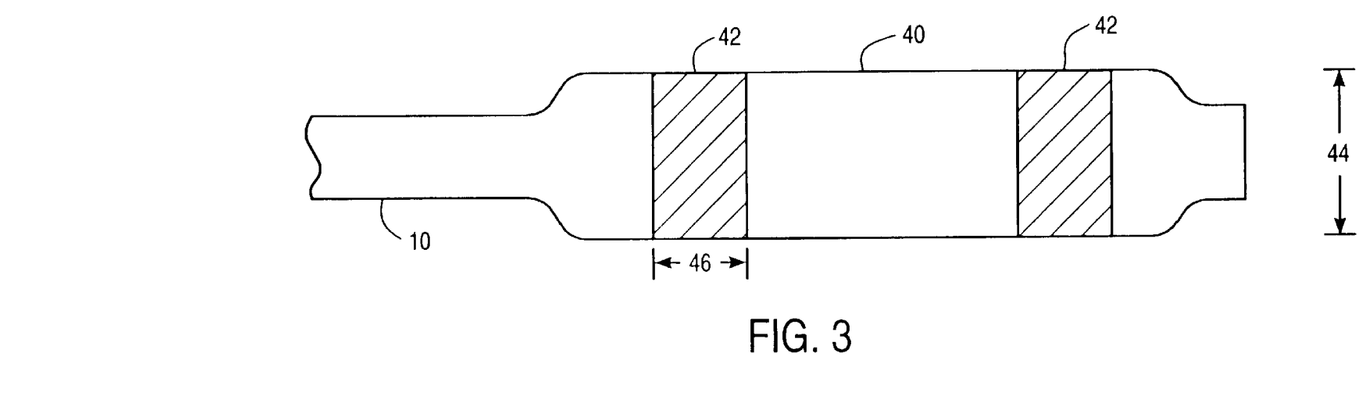
FIG. 3 illustrates a particular embodiment of the present catheter having elastomeric marking bands.
Figure 4:
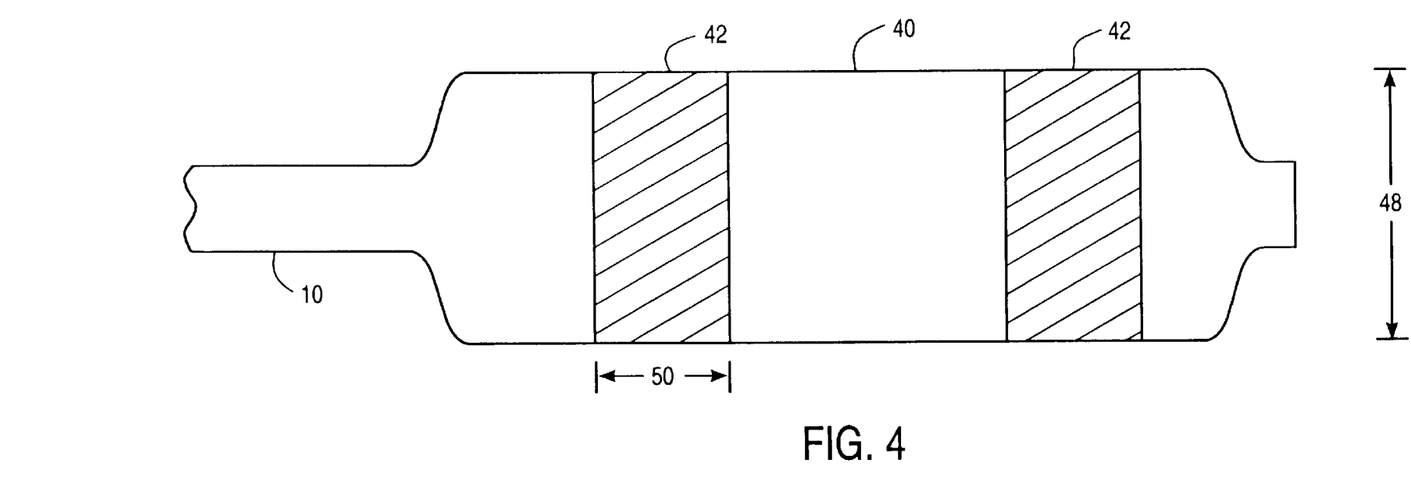
FIG. 4 illustrates the catheter of FIG. 3 with the balloon inflated.

FIGS. 3 and 4 illustrate an embodiment of the present lesion measurement catheter having marker bands for determining the inflated balloon circumference. Catheter 10 has a balloon 40 which is elastomeric. Balloon 40 includes two radiopaque elastomeric marker bands 42 attached to the surface of elastomeric balloon 40. FIG. 3 illustrates balloon 40 in a relaxed configuration having diameter 44, while bands 42 have relaxed width 46. Bands 42 will vary with the peripheral length of elastomeric balloon 40, which in turn will vary with balloon diameter when the balloon is not constrained. Generally, lesion measurement catheters according to the present invention will have a relaxed or unexpanded outer diameter in the range from 2 mm to 12 mm, preferably being in the range from 2 mm to 5 mm.

FIG. 4 illustrates balloon 40 in an expanded configuration, having an expanded diameter 48. Fully expanded lesion measurement balloons will have diameters in the range from 6 mm to 45 mm, preferably being in the range from 12 mm to 32 mm. As shown here, the expanded balloon remains unconstrained. Bands 42 of expanded balloon 40 have increased in diameter with the balloon, with a corresponding change in measured width 50. However, if the balloon was constrained during expansion by a lumen wall having an irregular cross-section, it will be understood that measured width 50 would vary with the balloon's circumference. Thus, a correlation may be drawn between measured width 50, and balloon circumference. Therefore, fluoroscopy or x-ray imaging which allows measurement of measured width 50 will also provide the circumference of expanded balloon 40.

Figure 5:
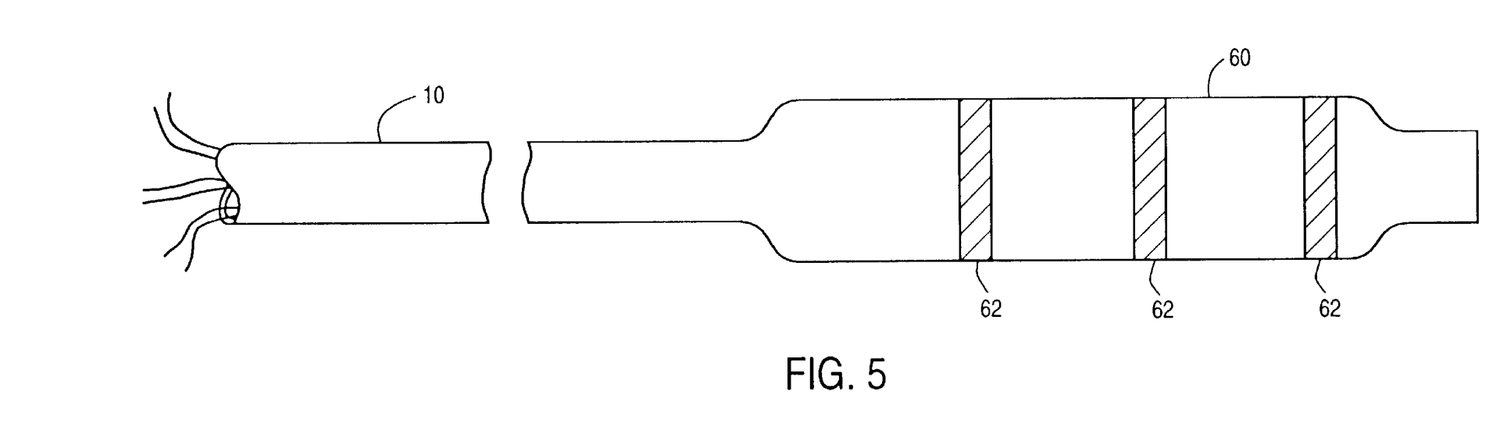
FIG. 5 illustrates an alternative embodiment of the present catheter having bands which vary in resistance with balloon circumference.
Figure 6:
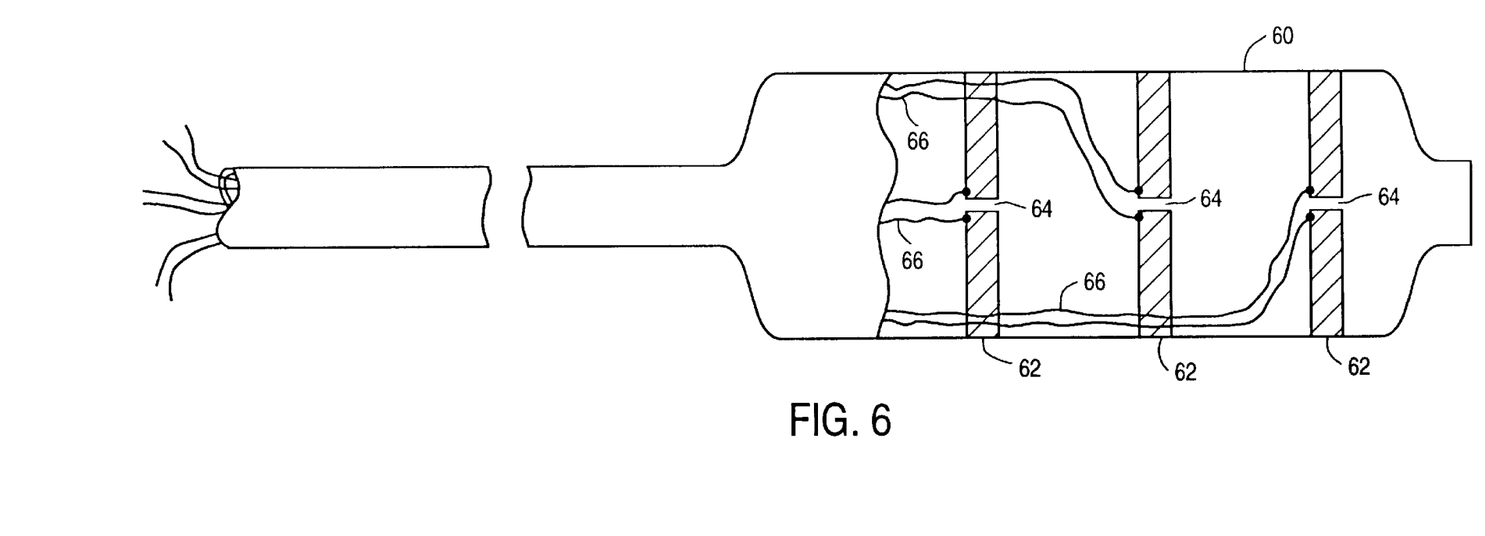
FIG. 6 is an interior view of the catheter of FIG. 5 with the balloon expanded.

FIGS. 5 and 6 illustrate an embodiment of the present lesion measurement catheter having conductor bands which vary in resistance with balloon circumference. FIG. 5 shows catheter 10 having balloon 60 with three elastomeric resistors 62. Resistors 62 are formed of a polymer or other elastomer having known conductive properties. Suitable materials will change in resistance in a predictable manner during elongation, such as polyisoprene with carbon black dispersion or polysiloxane foam with graphite impregnation.

FIG. 6 provides a cut-away view of the interior of balloon 60 in an expanded configuration. Elastomeric resistors 62 each have a gap 64 defining two resistor ends. A wire 66 is attached to each end of the resistor, and extends down the catheter body. As balloon 60 expands within the lumen, elastomeric resistors 62 predictably increase in length and resistance. Measurement of the electrical resistance while balloon 60 is expanded within the lumen allows calculation of the peripheral length of the expanded balloon. Alternatively, the resistors may be elastomeric segments which are attached to opposite sides of the inner balloon surface to define a diameter. Advantageously, the multiple resistors of this embodiment may be used to provide information on balloon cross-section in more than one target location.

Figure 7:
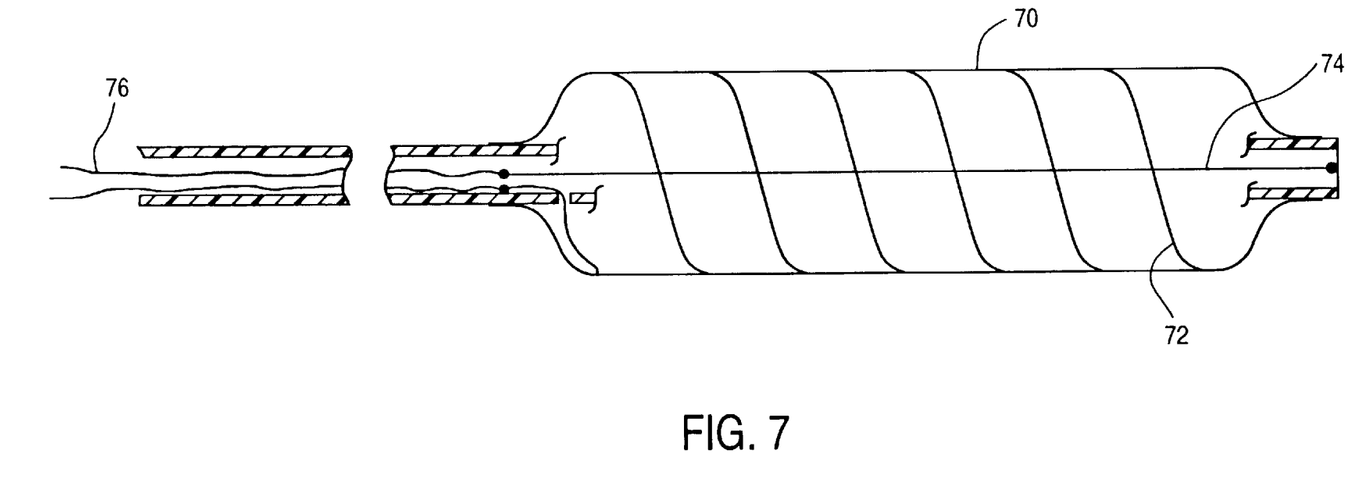
FIG. 7 illustrates an embodiment of the present catheter having an electrical coil which expands with the balloon.

FIG. 7 illustrates an alternative embodiment of a lesion measurement system in which balloon cross-section is measured based on changes in the electrical properties of a coil. A balloon 70 has a coil 72 which expands with the inflated balloon wall. Coil 72 may be elastomeric or may alternatively be a flexible wire riding in an elastomeric conduit, as will be described in regard to FIG. 9. Regardless, as the balloon is inflated, the electrical properties of coil 72 will change predictably. In some embodiments, a central wire 74 may be attached to the distal end of coil 72. The balloon circumference and diameter may be correlated from the coil resistance, inductance, or capacitance. Once again, a pair of wires 76 allow measurement while the catheter is inflated within the lumen.

Figure 8:
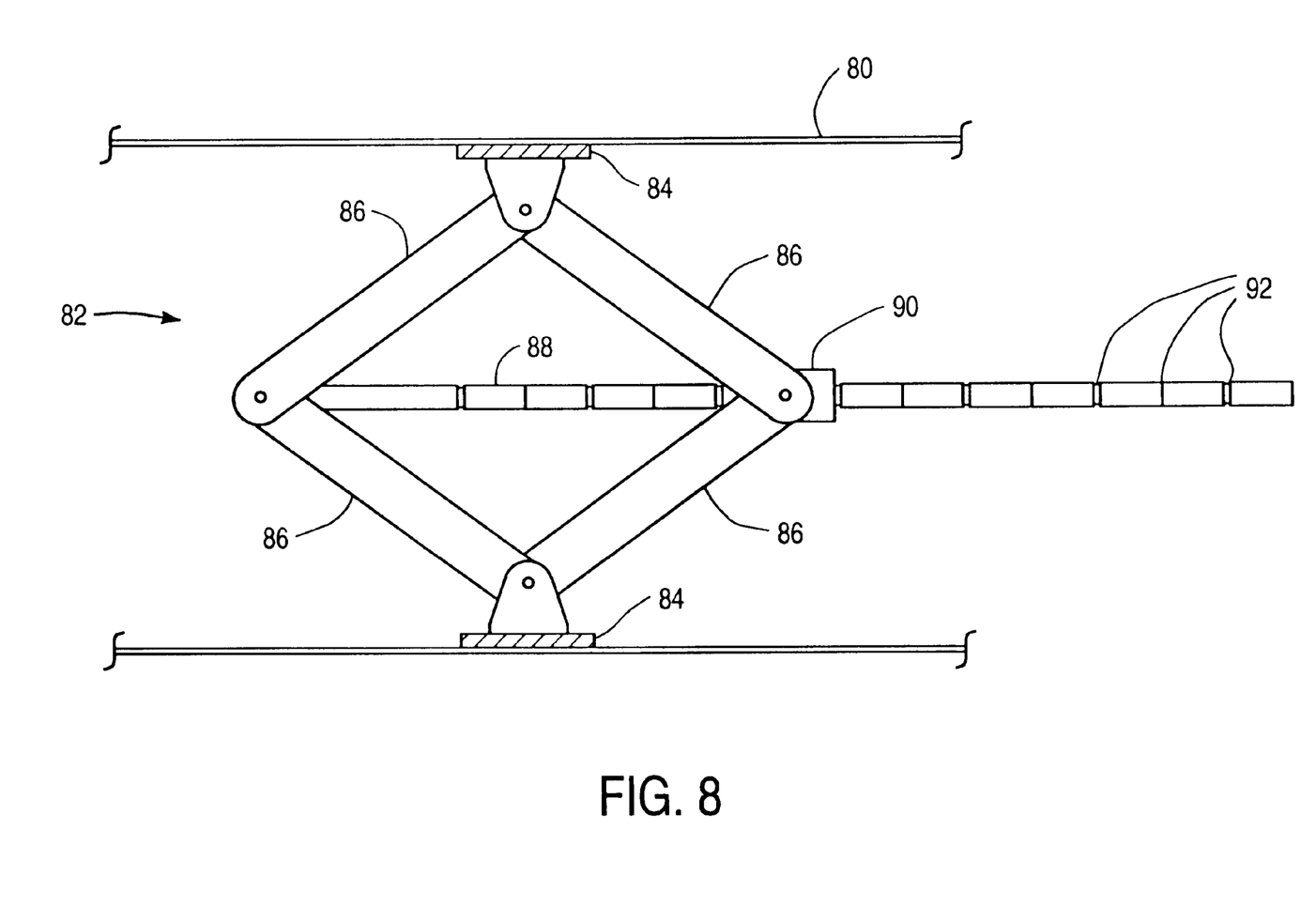
FIG. 8 illustrates a mechanical linkage which is attached to opposing sides of the inner surface of an alternative embodiment of the present catheter.

FIG. 8 illustrates a mechanical linkage for directly measuring balloon diameter in a further alternative embodiment of the present lesion measurement catheter. A balloon 80 contains a linkage 82 which is bonded to two pads 84 on opposite sides of the inner surface of balloon 80, thereby defining a diameter. Pads 84 support four equal length links 86 which are rotatably joined to form a parallelogram. A diagonal link 88 defines a diagonal of the parallelogram, and is held by a pivot at one end while the other end slides in a sleeve 90. The length of the parallelogram diagonal varies with balloon diameter, allowing balloon diameter to be read from the location of sleeve 90 relative to a set of calibrated radiopaque marking 92 on diagonal link 88. Balloon diameter could be read by fluoroscopy, for example. Alternatively, the diagonal link might extend down the catheter body to be read from a calibrated scale at the proximal end of the catheter. Clearly, a wide variety of alternative mechanical linkages could be used.

Figure 9:
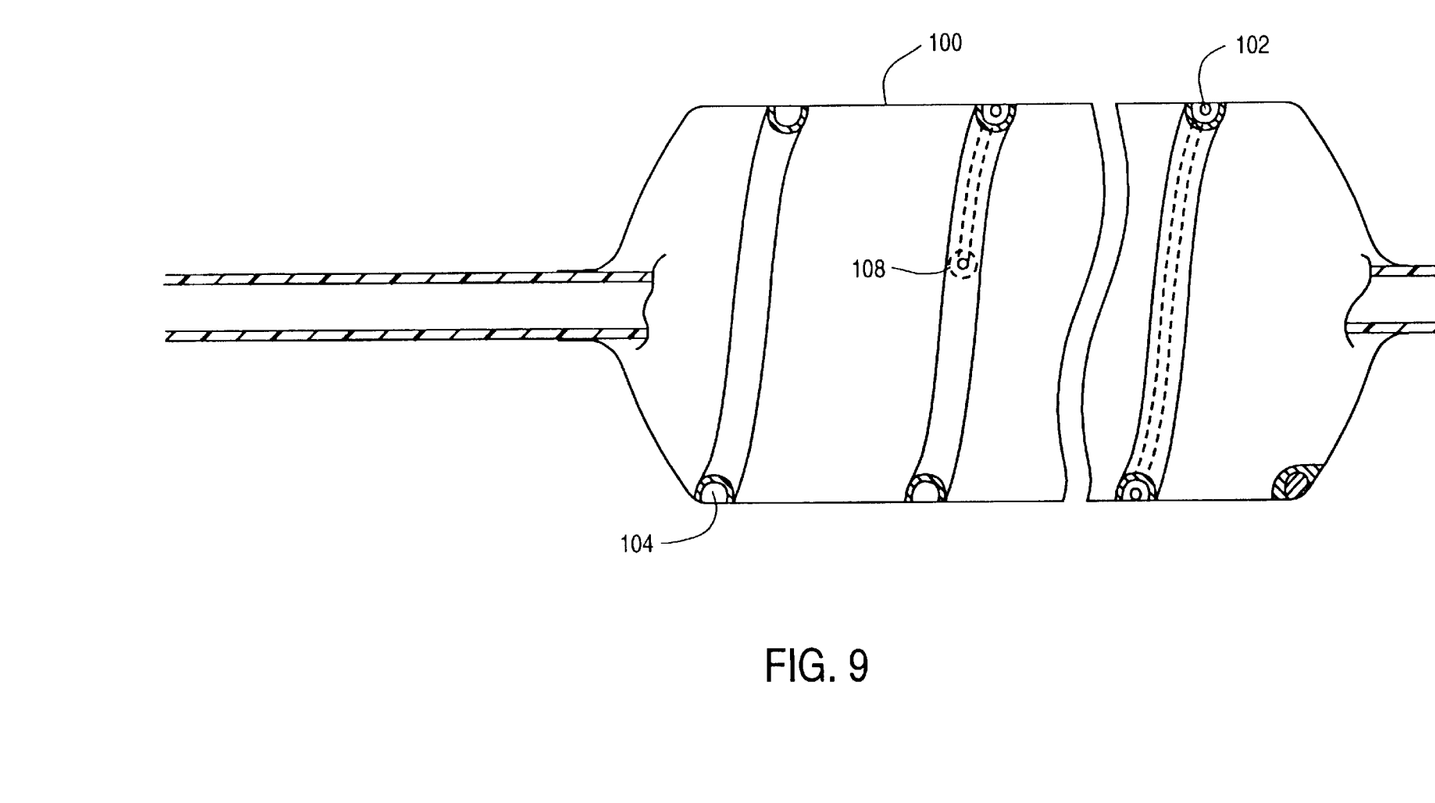
FIG. 9 illustrates an embodiment of the present lesion measurement catheter having a flexible conduit attached to the balloon and an inelastic wire disposed within the conduit.

FIG. 9 illustrates a further embodiment of the present lesion measurement catheter comprising a balloon 100 and a flexible, inelastic coil 102. Preferably, coil 102 is disposed within an open elastic conduit 104, which is bonded to balloon 100. As balloon 100 expands, conduit 104 increases in length, causing coil 102 to unwind. Preferably, one end of the coil is fixed within the conduit, allowing the peripheral length of the conduit to be determined by the position of the free end 108. Optionally, the coil may be formed of a material which provides a sharp image, allowing the coil windings or end position to be monitored by fluoroscopy, radiography, or ultrasound. Alternatively, where the distal end of the coil is fixed, the coil may extend down the catheter to provide an indication of the balloon circumference at the proximal end.

As can be seen in the embodiment of FIG. 9, the catheters of the present invention may advantageously include at least one lumen extending through the balloon. Such a lumen may provide access for a guide wire for repositioning the balloon, or other know intravascular devices. Preferably, such a lumen may allow introduction of an ultrasonic intravascular probe, as is shown in copending patent application Ser. No. 08/380,735 (Attorney Docket No. 16380-16), previously incorporated by reference. A separate inflation lumen may also be provided (not shown).

Figure 10:
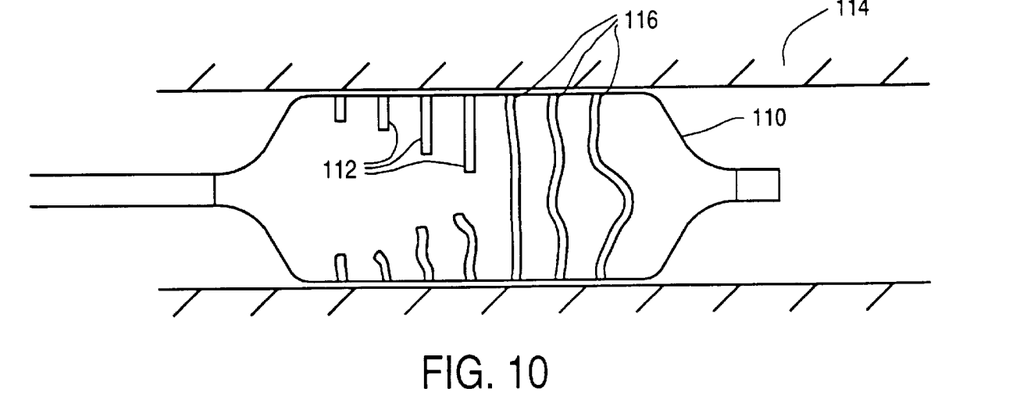
FIG. 10 illustrates an embodiment of the present catheter having a plurality of measurement elements.

FIG. 10 illustrates a still further embodiment of the present lesion measurement catheter, in which a balloon 110 has a plurality of measurement elements of varying length. The measurement elements may be in the form of segments attached to opposite sides of the balloon wall to define a plurality of diameters. Alternately, the elements may be disks or the like. At least one smaller segment 112 corresponds to a diameter smaller than the diameter of the target region of a lumen 114 to be measured, while at least one larger segment 116 is longer. As balloon 110 is inflated to match the body lumen diameter, smaller segments 112 will be broken, while larger segments 116 remain intact. Optionally, the segments would be of a type which would allow visualization by known visualization modalities. Alternatively, the maximum diameter of the inflated balloon can be determined or confirmed after the catheter is removed.

Figure 11:
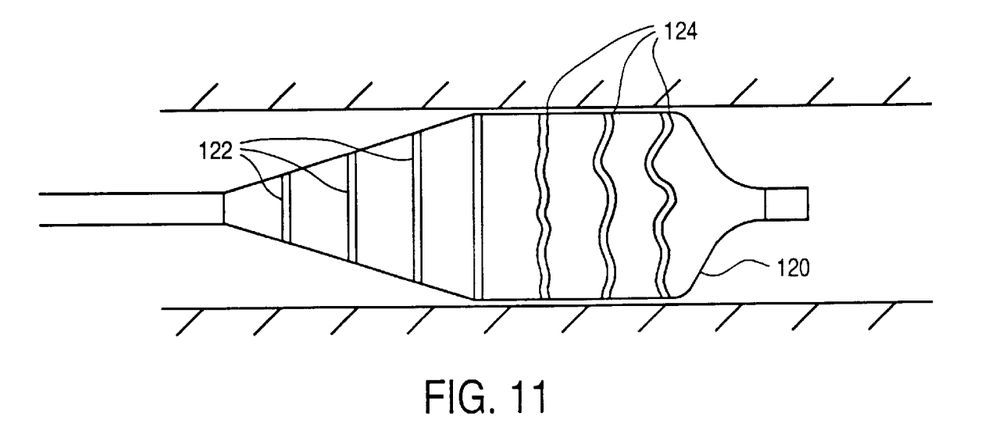
FIG. 11 illustrates an embodiment of the present catheter having a tapered balloon and a plurality of measurement elements.

FIG. 11 illustrates a lesion measurement catheter having a conical balloon 120. A plurality of measurement elements are provided, which may be similar to those described regarding FIG. 10, or may advantageously be simple marker rings which provide an image under fluoroscopy or ultrasound, optionally comprising gold or barium sulfate. Once again, at least one smaller ring 122 and at least one larger ring 124 are provided. Preferably, balloon 120 is inelastic, and is allowed to expand under low pressure until restrained by a lumen 126, as described above. The smaller rings 122 are fully expanded, while larger rings 124 are not. When visualized, the image of smaller rings 122 are straight and crisp, while larger segments 124 are wavy and indistinct. Advantageously, such a balloon would not suffer irreversible changes, and would therefore be reusable.

Figure 12:
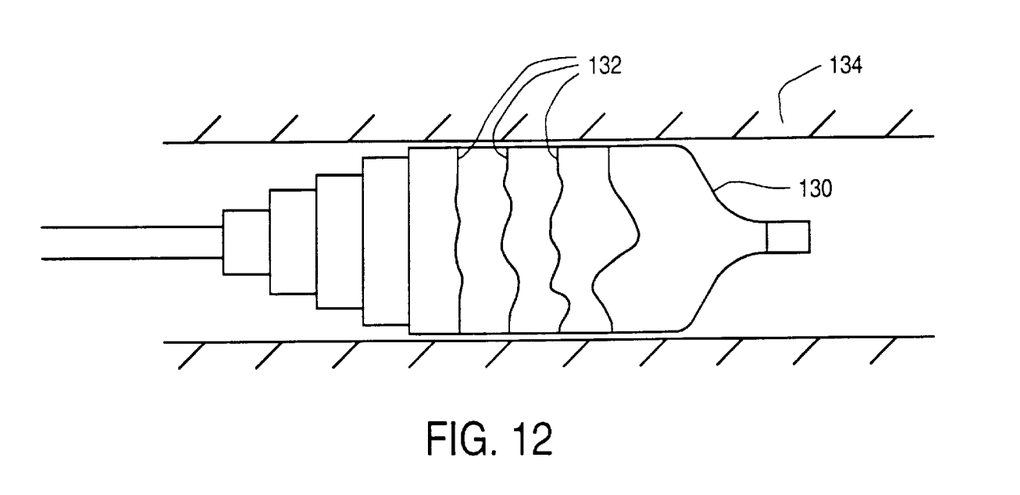
FIG. 12 illustrates an embodiment of the present catheter having a segmented balloon with rupture disks between segments.

FIG. 12 illustrates a final embodiment of the present lesion measurement catheter, in which a flexible segmented balloon 130 includes a plurality of bursting disks 132 of varying sizes. Each disk sequentially bursts under tension as the segments expand under low pressure to fill a body lumen 134. Segments larger than the lumen do not rupture their associated disks, as the lumen walls absorb the outward load. The lumen diameter is thus between the largest burst disk and the smallest intact disk. The intact disks optionally prevent the inflation fluid from flowing into the next larger segment, allowing balloon diameter to be measured by incremental fluid volume. Preferably, a radiopaque fluid is retained behind the intact disks, providing a clear indication of the lumen diameter by the number of filled segments, as seen under fluoroscopy, radiography, or ultrasound.

Although the foregoing invention has been described in some detail by way of illustration and example, for purposes of clarity of understanding, it will be obvious that certain changes and modifications may be practiced within the scope of the appended claims.

What is claimed is:

1. A body lumen cross-sectional dimension measurement catheter comprising:

a catheter body having a proximal end, a distal end, and a lumen between the proximal end and the distal end; and a balloon disposed about the distal end of the catheter body, the balloon in communication with the lumen; and a conductor attached to the balloon wall, which conductor varies in an electrical property in correlation with a cross-sectional dimension of the balloon.

2. A catheter as claimed in claim 1, wherein the conductor comprises a circumferential band, and wherein a resistance of the band varies with a balloon circumference.

3. A catheter as claimed in claim 1, wherein the conductor comprises a coil, and wherein the electrical property is selected from the group containing resistance, capacitance, and inductance.

4. A catheter as claimed in claim 3, wherein the coil is an elastomeric conductor.

5. A catheter as claimed in claim 3, wherein the coil is disposed in a conduit attached to the balloon wall.

6. A body lumen cross-sectional dimension measurement catheter comprising:

a catheter body having a proximal end, a distal end, and a lumen between the proximal end and the distal end;

a balloon disposed about the distal end of the catheter body, the balloon in communication with the lumen and defining a cross-sectional dimension that varies as the balloon is inflated; and a measurement element engaging a wall of the balloon, the measurement element transmitting a signal proximally along the catheter body, the signal indicating the cross-sectional dimension of the inflated balloon.

7. A catheter as claimed in claim 6, wherein the measurement element varies in electrical property with the cross-sectional dimension of the balloon, the signal comprising an electrical signal.

8. A catheter as claimed in claim 6, wherein the measurement element effects movement between the catheter body and an elongate signal structure extending proximally from the measurement element along the catheter body, the signal comprising a mechanical signal.

* * * * *